United States Patent [19]

O'Sullivan et al.

[11] Patent Number: 5,081,225
[45] Date of Patent: Jan. 14, 1992

[54] **GRAM-POSITIVE AND GRAM-NEGATIVE ANTIBACTERIAL COMPOUNDS FROM THE MICROORGANISM, *JANTHINOBACTERIUM LIVIDUM***

[75] Inventors: Joseph O'Sullivan, Belle Mead; John E. McCullough, Whitehouse Station; Janice H. Del Mar, Hopewell, all of N.J.

[73] Assignee: E. R. Squibb & Sons, Inc., Princeton, N.J.

[21] Appl. No.: 388,089

[22] Filed: Jul. 31, 1989

Related U.S. Application Data

[63] Continuation-in-part of Ser. No. 310,118, Feb. 9, 1989, abandoned.

[51] Int. Cl.⁵ ............................................. C07K 7/54

[52] U.S. Cl. .................................................... 530/317
[58] Field of Search ............... 530/317, 323; 424/115, 424/118, 119, 120, 121, 122

[56] References Cited

U.S. PATENT DOCUMENTS 4,294,754  10/1981  Takahara et al. .................. 530/317
4,754,018   6/1988  Tymiak et al. ..................... 530/317

*Primary Examiner*—F. T. Moezie
*Assistant Examiner*—Christina Chan
*Attorney, Agent, or Firm*—Theodore R. Furman, Jr.

[57] ABSTRACT

A novel antibiotic substance, janthinocin, is prepared by cultivation of a strain of the microorganism *Janthinobacterium lividum*, ATCC No. 53,857.

7 Claims, 13 Drawing Sheets

GRAM-POSITIVE AND GRAM-NEGATIVE ANTIBACTERIAL COMPOUNDS FROM THE MICROORGANISM, *JANTHINOBACTERIUM LIVIDUM*

This is a continuation-in-part of U.S. Ser. No. 310,118 filed Feb. 9, 1989, now abandoned.

SUMMARY OF THE INVENTION

Cultivation of a strain of the microorganism *Janthinobacterium lividum* which has been deposited in the American Type Culture Collection as A.T.C.C. No. 53,857 yields a novel class of antibiotics hereinafter referred to by the trivial chemical names "janthinocin A, B, and C." Janthinocin A, B, and C have activity against Gram-positive and Gram-negative bacteria and anaerobic bacteria. Janthinocin has been analyzed and found to have the following general chemical structure:

I.

wherein Δ-Abu is dehydro-α-aminobutyric acid;
βHL is D-erythro-β-Hydroxyleucine;
and further wherein X is β-Hydroxytryptophan for janthinocin A;
X is β-ketotryptophan for janthinocin B;
X is dehydrotryptophan for janthinocin C.

In solution, the η-keto-tryptophan residue of janthinocin B exists as a mixture of geometric isomers, that is as the E and Z enols of β-ketotryptophan, hereinafter janthinocin $B_1$ and $B_2$. The two isomers are separable chromatographically, but slowly interconvert to give a pH and solvent dependent equilibrium mixture. The two isomers are referred to in the text as janthinocin $B_1$ and $B_2$.

DETAILED DESCRIPTION OF THE INVENTION

The Microorganism

Figure 1:
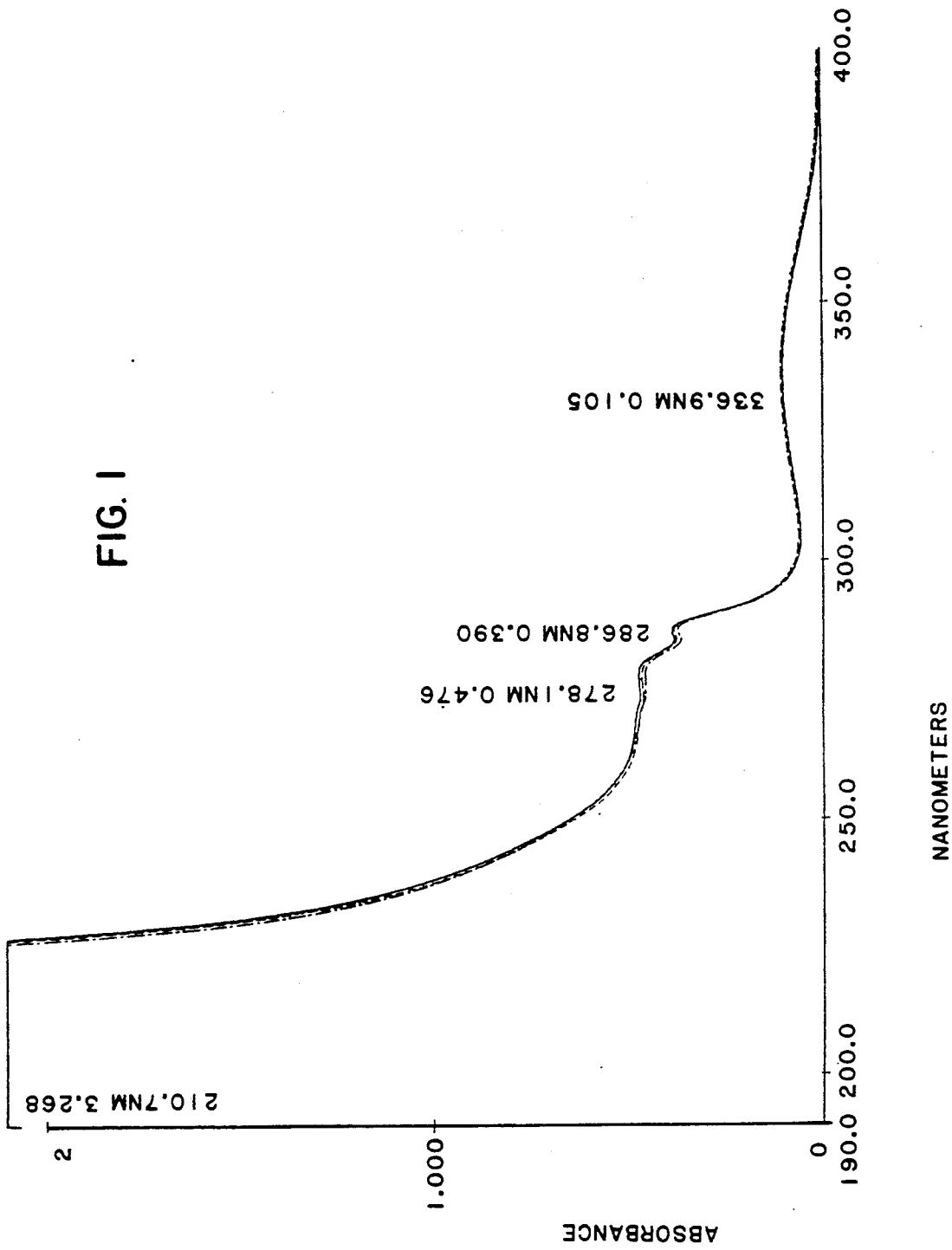
FIG. 1 shows the ultraviolet spectrum of janthinocin A in water and in 0.01M HCl and 0.01M NaOH.

The microorganism used for the production of janthinocins A, B and C is a strain of *Janthinobacterium lividum* isolated from stagnant water collected in Tyler State Park, Newtown, PA. A subculture of the organism can be obtained from the American Type Culture Collection, Rockville, MD. Its accession number in this repository is A.T.C.C. No. 53,857.

In addition to the specific microorganism described and characterized herein, it should be understood that mutants of the microorganism produced through the use of chemical or physical mutagens can also be cultivated to produce the product.

The culture of *Janthinobacterium lividum* can be isolated from the stagnant water sample by preparing a suitable dilution in a medium consisting of the following:

|  | Gram |
| --- | --- |
| NaCl | 8.5 |
| $KH_2PO_4$ | 0.3 |
| $Na_2HPO_4$ | 0.6 |
| Gelatin | 0.1 |

0.1 ml of this material was plated onto agar plates containing:

|  | Measure |
| --- | --- |
| Peptone | 1 g |
| $K_2HPO_4$ | 0.2 g |
| Glucose | 1 g |
| 1% Crystal Violet | 0.1 ml |
| Soil extract | 1 liter |
| Agar | 15 g |

The pH is adjusted to 6.8 and the mixture autoclaved at 121° C. for 15 minutes. Ten ml of a 1% (W/V) cycloheximide solution is then added to a liter of medium. The soil extract is prepared as follows: 1000 ml soil is boiled in 2 liters of water for 1 hour. The solids are filtered out through cheesecloth and the solution then centrifuged for 20 minutes at 28,000 rpm. The supernatant is then filtered through Whatman paper and autoclaved for 30 minutes at 121° C.

The organism is a motile Gram negative bacterium that is rod-shaped with sub-polar to lateral flagella. Colonies on nutrient agar are gelatinous and dark purplish-black in color. The gelatinous material is extracellular polysaccharide; the pigment produced is violacein. Glucose is utilized oxidatively. Acid is produced from trehalose but not from l-arabinose or d-xylose. The organism is negative for arginine dihydrolase, production of HCN and esculin hydrolysis. The bacterium is identified as an aberrant strain of Janthinobacterium lividum.

The Antibiotic Janthinocin

The antibiotic janthinocin can be produced by cultivating Janthinobacterium lividum, A.T.C.C. No. 53,857 at, or near, 25° C. under submerged aerobic conditions in an aqueous nutrient medium containing assimilable carbohydrate and nitrogen sources. The fermentation is carried out until substantial activity is imparted to the medium, usually about 24 to 28 hours.

After fermentation solid ammonium sulfate is added (25% wt/v) to the whole broth, the broth is centrifuged and the resulting pellet is extracted with methanol. The methanol-pellet mixture is centrifuged and the resulting methanol extract is made approximately 10% aqueous by the addition of water, and then extracted with carbon tetrachloride. The layers are separated and the methanol extract delivered for isolation.

The methanol extract is added to MCI GEL CHP20P ™ (CHP20P) in water and the mixture is stirred for one hour. The charged resin is collected by vacuum filtration and washed with methanol, water, and acetonitrile. The charged resin is then packed in a column and the antibiotics are eluted with acetonitrile-water-formic acid. Further purification is achieved by chromatography on SEPHADEX LH-20 ™ in acetonitrile-water. Partial resolution of the three antibiotics, janthinocin A, B, and C, is effected by chromatography on CHP20P eluting with a gradient of acetonitrile-water-formic acid. Final separation and purification of janthinocins B and C is achieved by chromoagraphy on CHP20P eluting with an acetonitrile-aqueous ammonium dihydrogen phosphate buffer gradient, followed by desalting on CHP20P, eluting with acetonitrile-water-formic acid, to give the pure antibiotics as off white powders. The amount of janthinocin C in the fermentations is variable, and its presence may be an artifact of the isolation conditions (janthinocin A is converted to janthinocin C under acidic conditions). When janthinocin C is present, it co-elutes with janthinocin B in each of the initial chromatographies.

Figure 2:
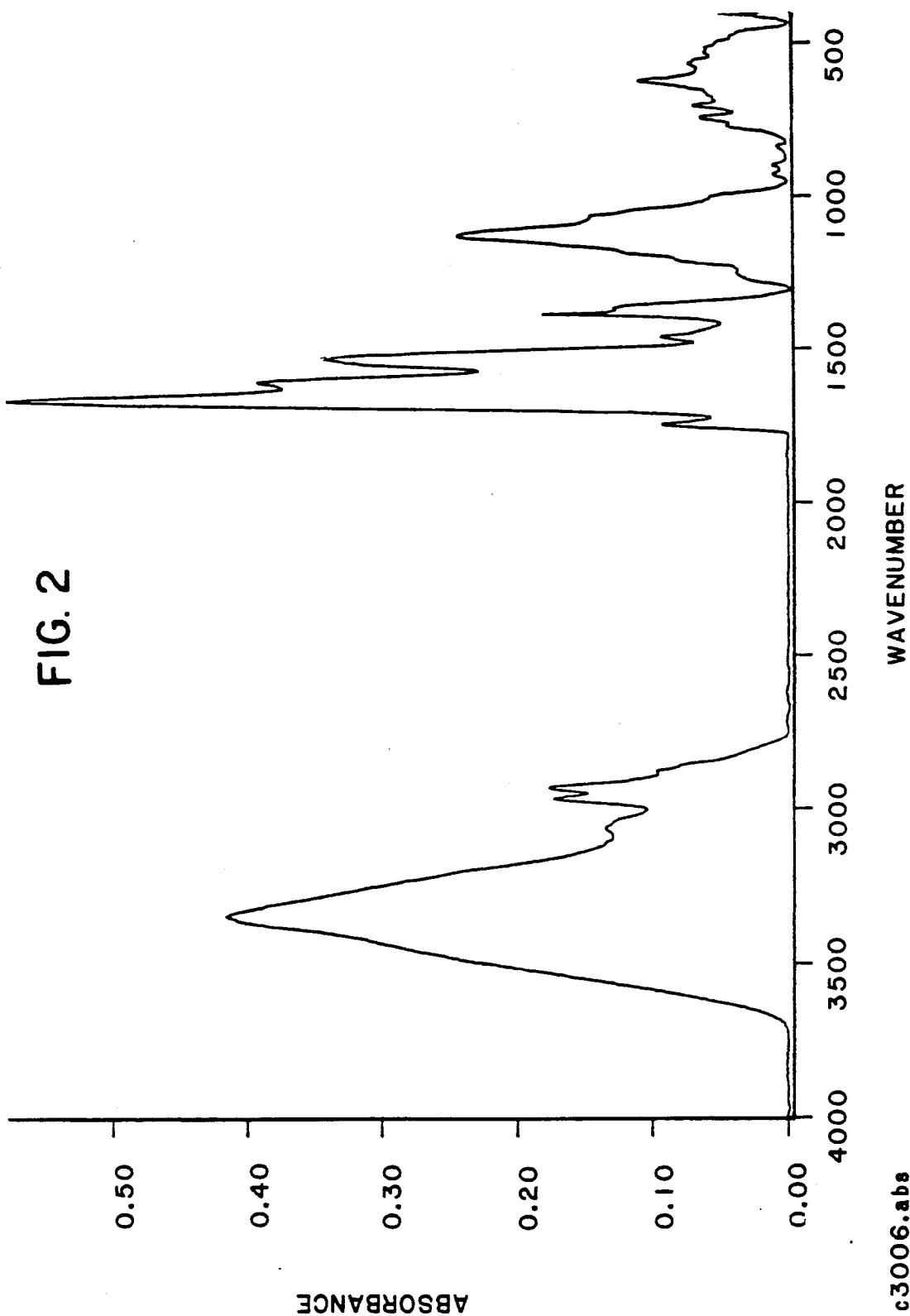
FIG. 2 shows the infrared spectrum of janthinocin A in potassium bromide.
Figure 3:
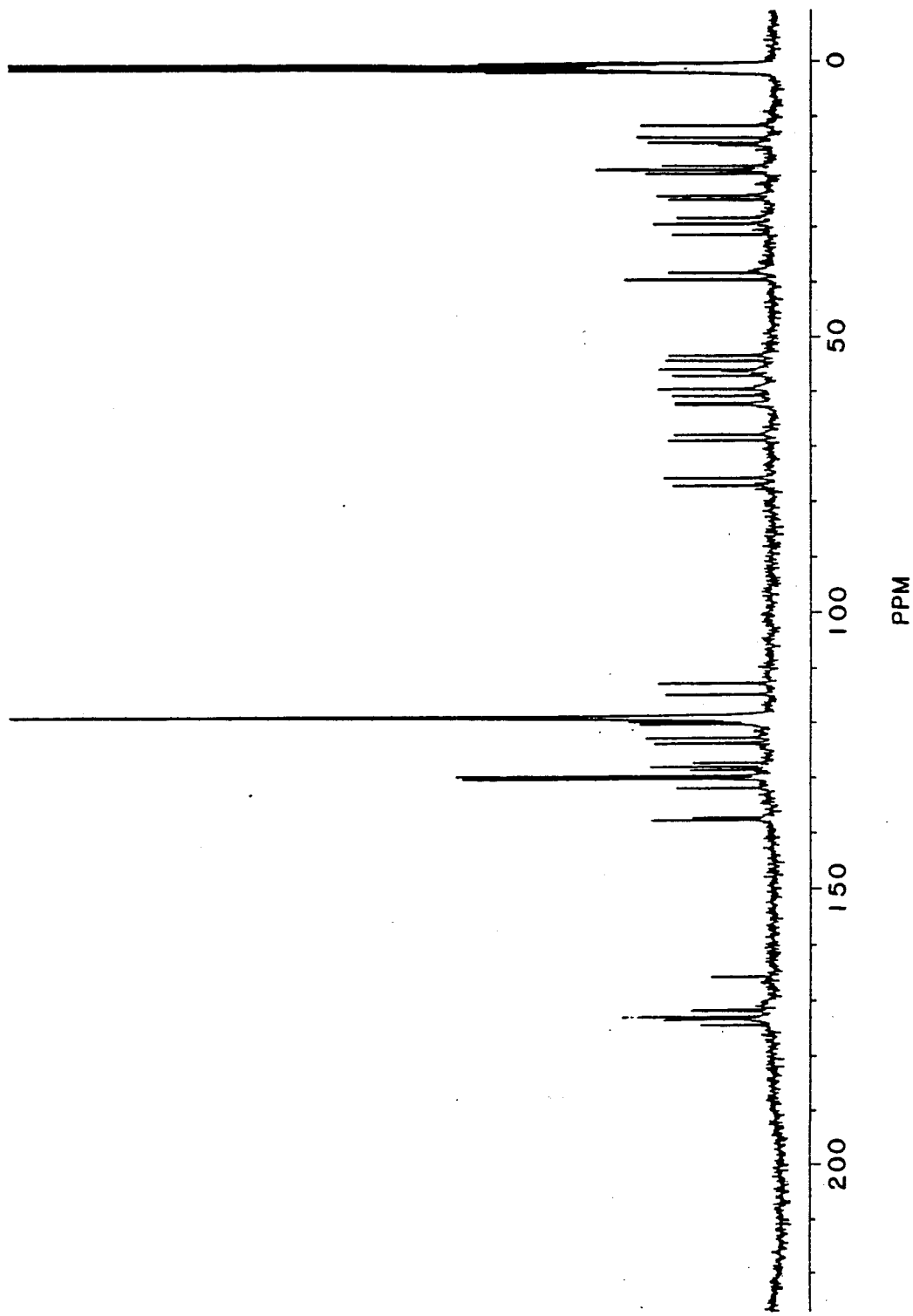
FIG. 3 shows the 67.5 MHz carbon NMR spectrum of janthinocin A in deuterated acetonitrile-deuterated water (1:4).
Figure 4:
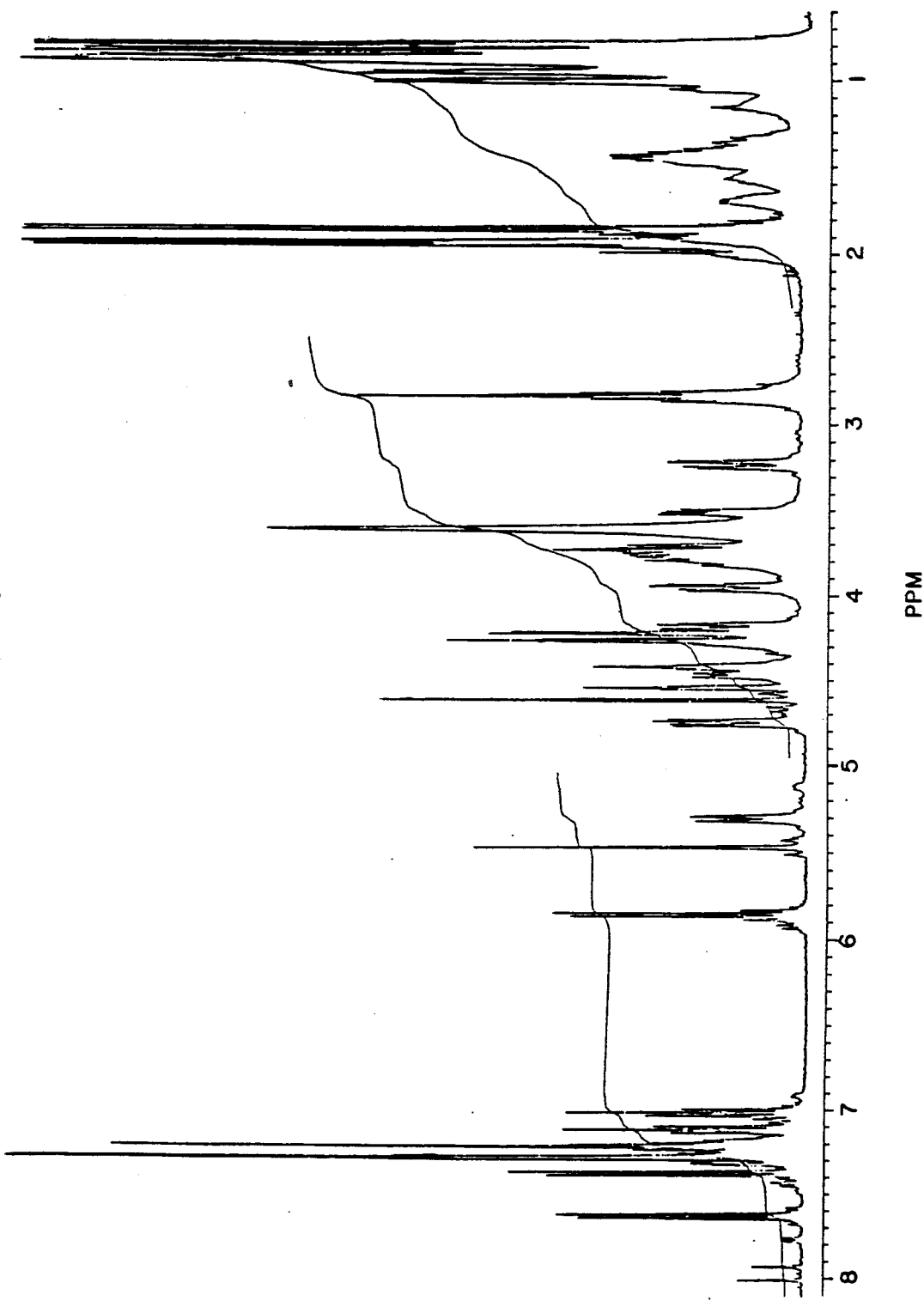
FIG. 4 shows the 400 MHz proton NMR spectrum of, janthinocin A in deuterated acetonitrile-deuterated water (4:1).

The ultraviolet spectrum of janthinocin A is given in FIG. 1 and shows: λmax ($E^{1\%}$ 1 cm) 337(8), 287(30), 276(36), 204 nm (270). The infrared spectrum of janthinocin A in potassium bromide is shown in FIG. 2. The following peaks are evident: 3342, 2962, 1743, 1659, 1602, 1525, 1383, and 1126 cm$^{-1}$. The FAB mass spectrum of janthinocin A in dithiothreitol-dithioerythritol-dimethylsulfoxide-glycerol with added sodium iodide shows the following ions: $(M+Na)^+$ 1215, $(M+H)^+$ 1193 (weak), $(M+H-H_2O)^+$ 1175, $(M+I)^-$ 1319. Without added sodium iodide, only the $(M+H-H_2O)+1175$, and $(M-H-H_2O)^-$ ions are seen. The 67.5 MHz $^{13}$C NMR spectrum of janthinocin A in deuterated acetonitrile-deuterated water (1:4) is shown in FIG. 3. The 400 MHz $^1$H NMR spectrum of janthinocin A in deuterated acetonitrile-deuterated water (4:1) is shown in FIG. 4. Thin layer chromatography of janthinocin A on MERCK SILICA GEL-60 ™ using chloroform-methanol-70% aqueous ethanol, 7:3:5, gives an $R_f$ value of 0.38. High performance liquid chromatography of janthinocin A on a HAMILTON PRP-1 ™ column (150×4.1 mm), eluting with Buffer A at 1 ml/min., and monitoring the absorbance at 220 nm, gives a retention time of 3.90 min. Buffer A is $CH_3CN-H_2O$ (33:67), 1% in $NH_4H_2PO_4$ adjusted to pH 3.6 with 85% $H_3PO_4$.

Figure 5:
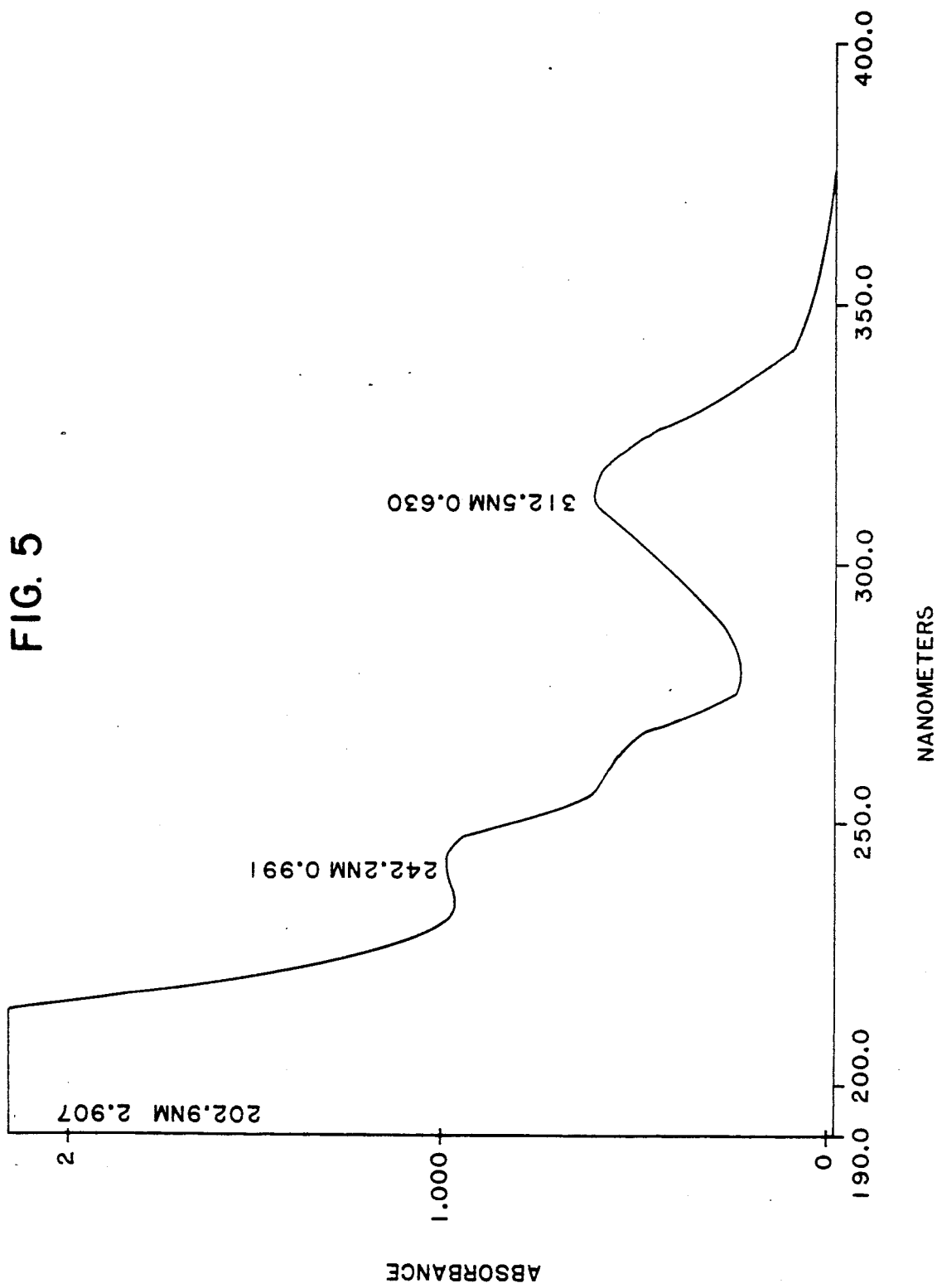
FIG. 5 shows the ultraviolet spectrum of janthinocin B in water.
Figure 6:
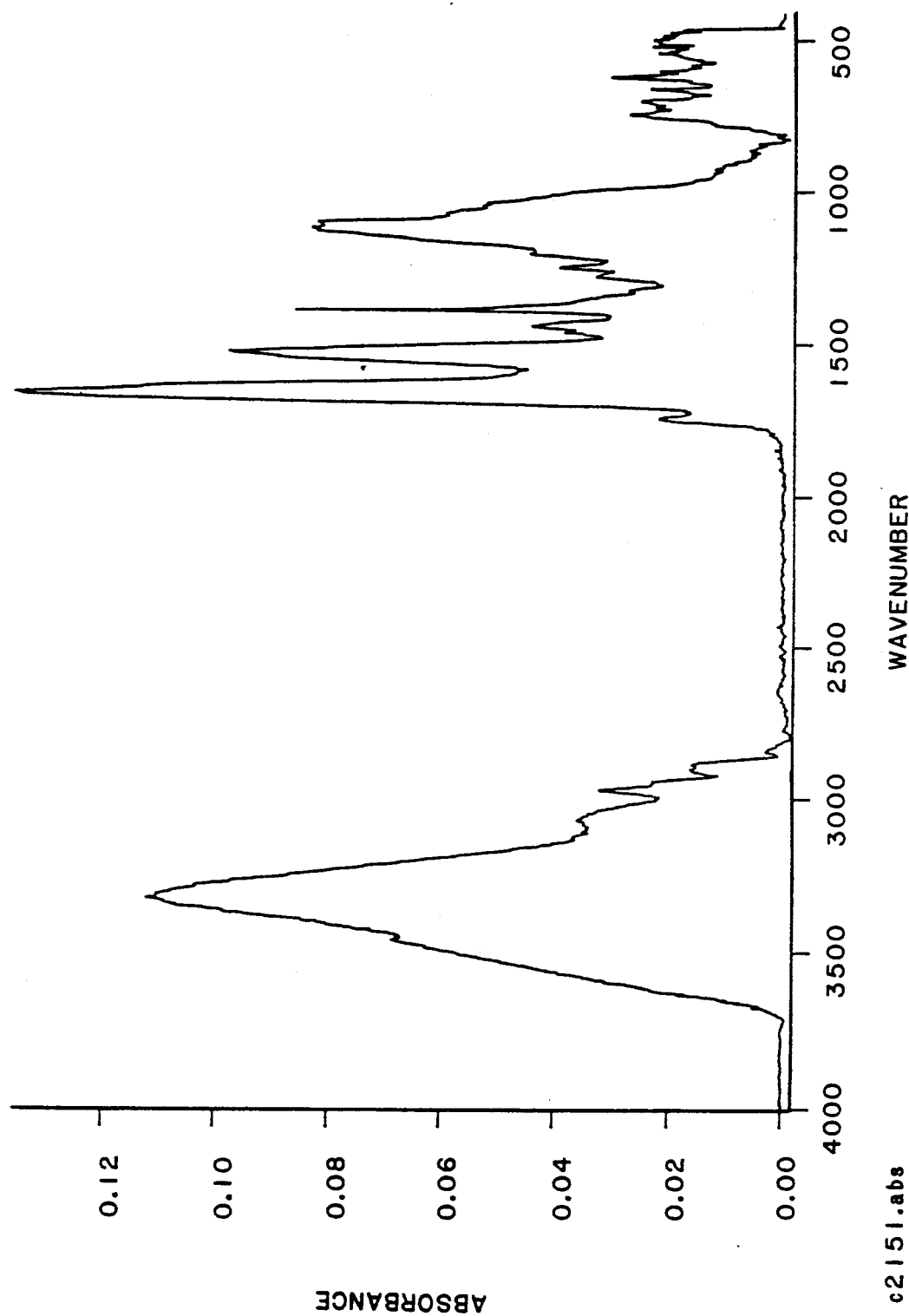
FIG. 6 shows the infrared spectrum of janthinocin B in potassium bromide.
Figure 7:
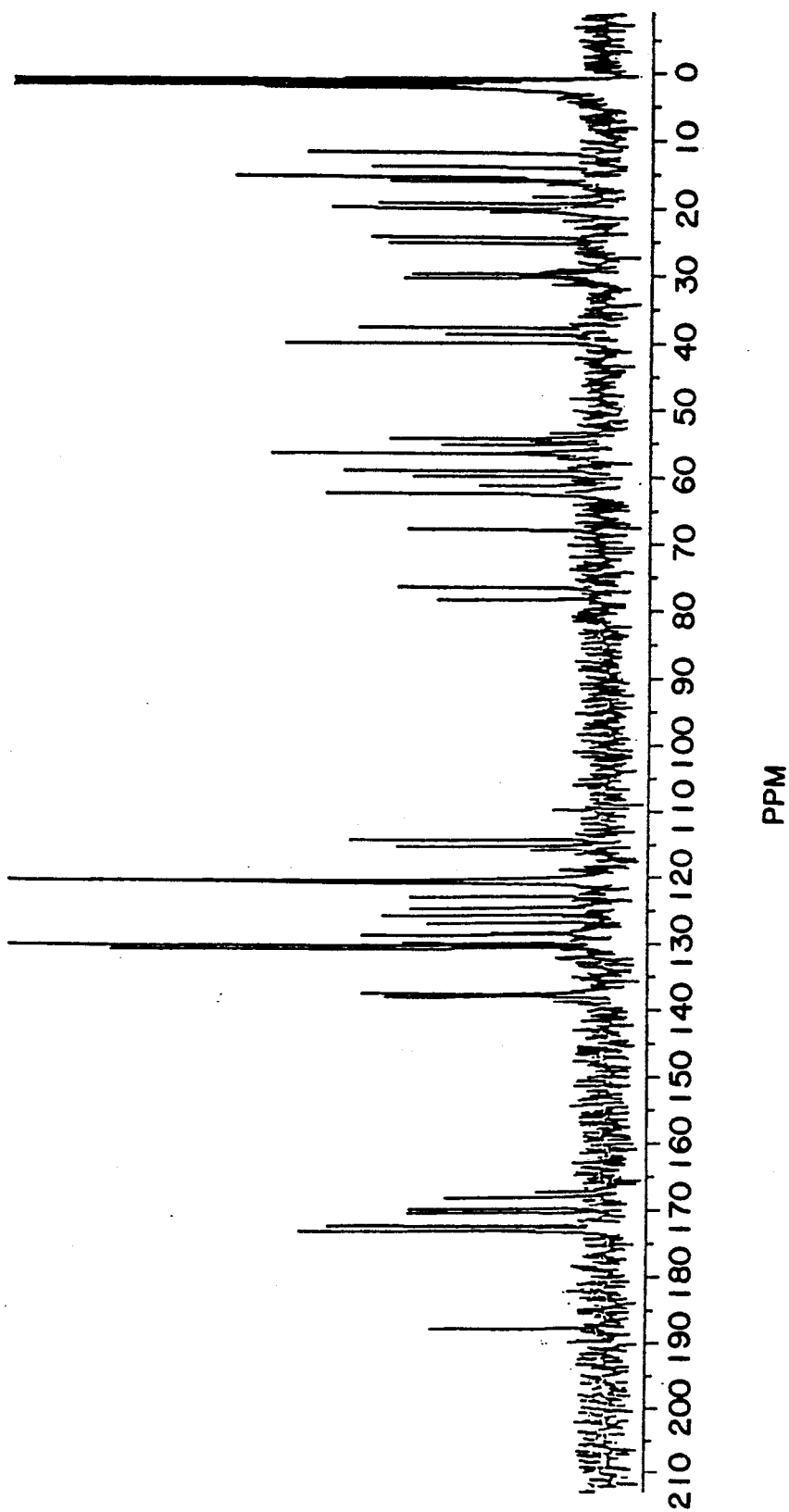
FIG. 7 shows the 67.5 MHz carbon NMR spectrum of janthinocin B ($B_1$:$B_2$ about 3:1) in deuterated acetonitrile-deuterated water (1:4).
Figure 8:
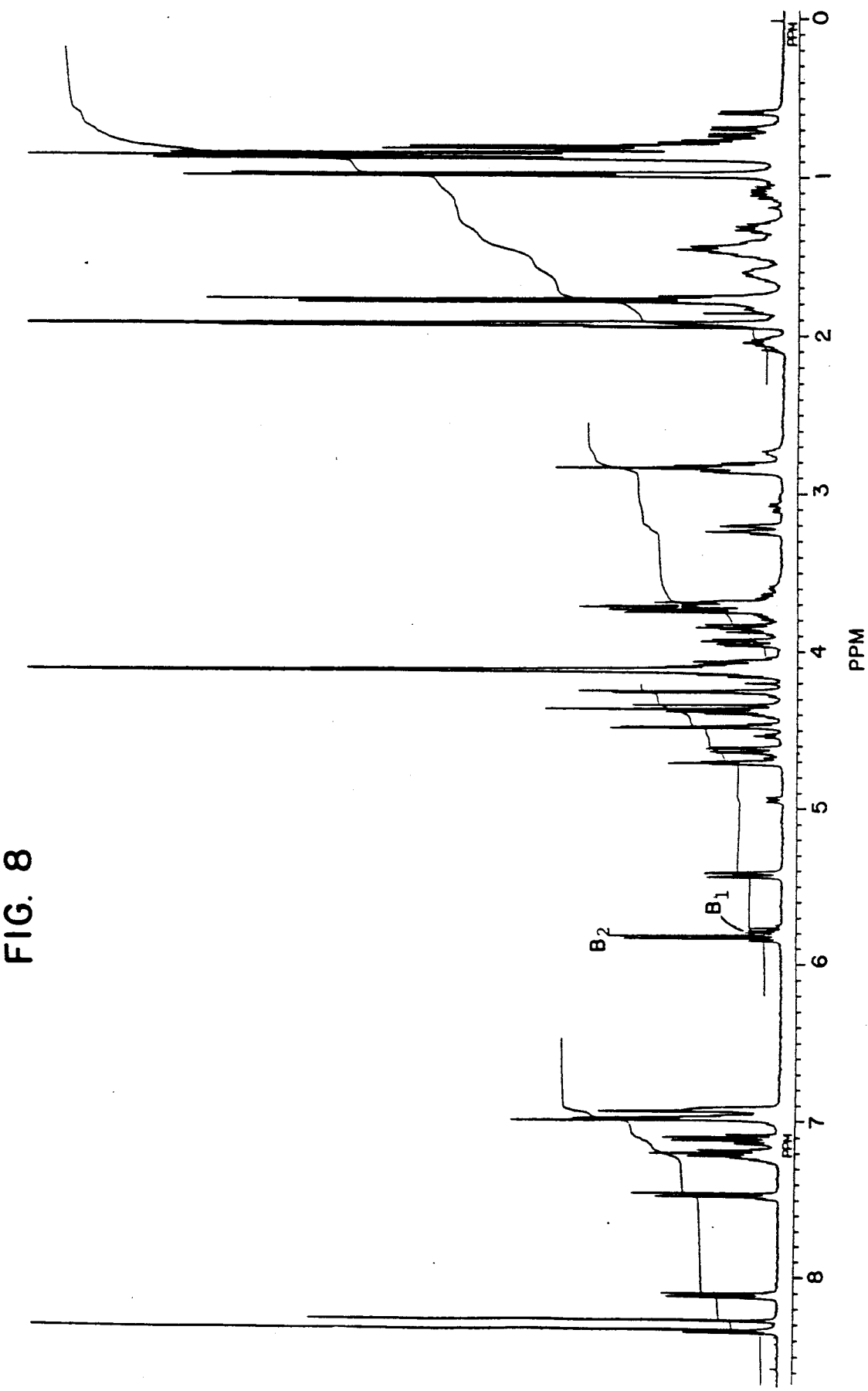
FIG. 8 shows the 400 MHz proton NMR spectrum of janthinocin B ($B_2$:$B_1$ about 4:1) in deuterated acetonitrile-deuterated water (1:1, pH 7.1 with $Na_2DPO_4$).
Figure 9:
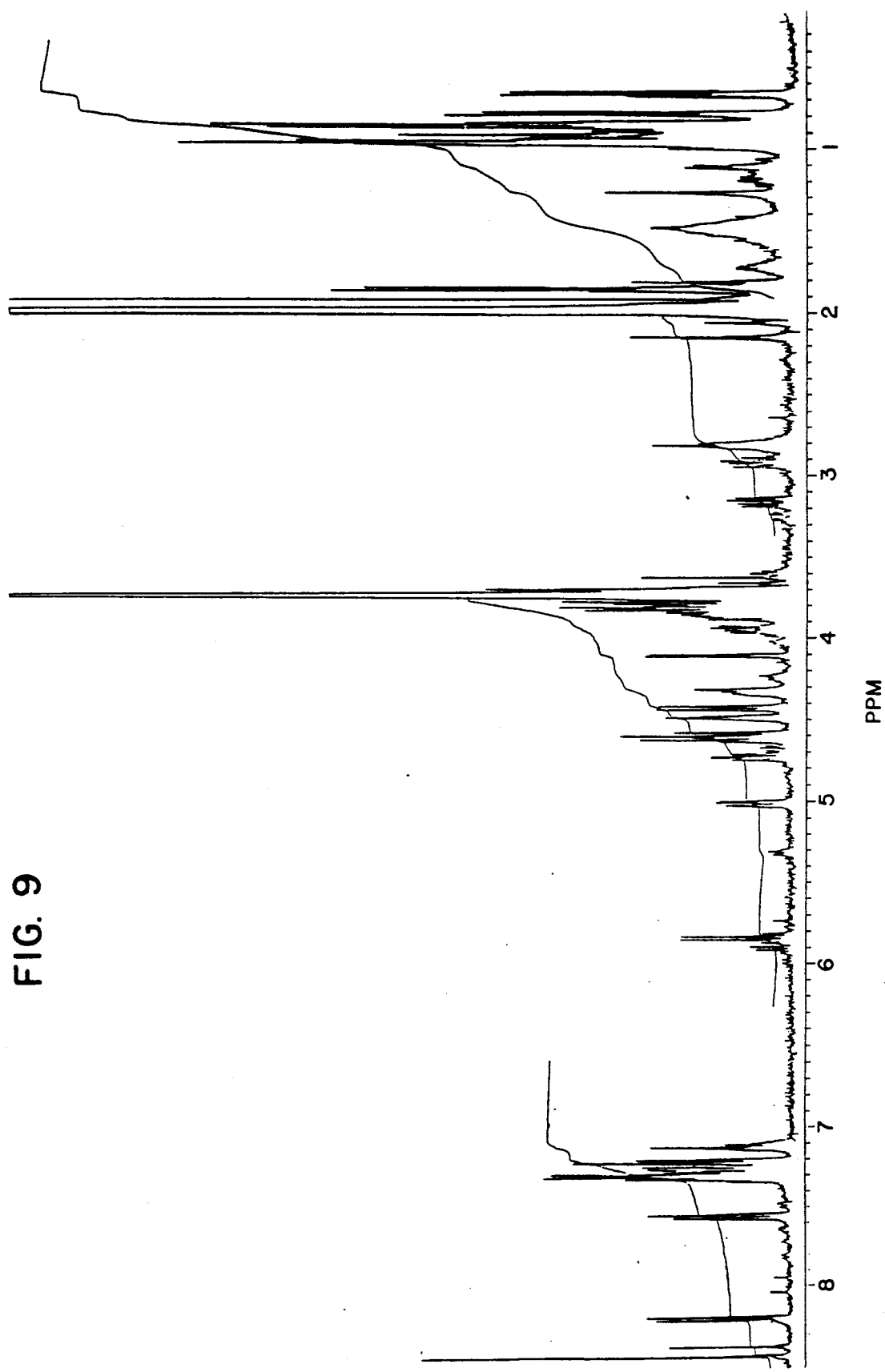
FIG. 9 shows the 400 MHz proton NMR spectrum of janthinocin B ($B_2$:$B_1$ about 1:4) in deuterated acetonitrile-deuterated water (4:1).

The ultraviolet spectrum of janthinocin B is given in FIG. 5 and shows: λmax ($E^{1\%}$ 1 cm) 312(82), 260(sh), 242(120), 204 nm, (350). The infrared spectrum of janthinocin B in potassium bromide is shown in FIG. 6. The following peaks are evident: 3322, 3066, 2967, 1742, 1655, 1522, 1384, 1116 cm$^{-1}$. The FAB mass spectrum of janthinocin B in dithiothreitol-dithioerythritoldimethylsulfoxide-glycerol with added sodium iodide shows the following ions: $(M+Na)^+$ 1213, $(M+H)^+$ 1191, $(M+I)^-$ 1317. Without added sodium iodide, only the $(M+H)^+$ 1191 and $(M-H)^-$ 1189 ions are seen. The high resolution FAB mass spectrum shows an $(M+H)^+$ of 1191.6142 consistent with the molecular formula $C_{57}H_{83}N_{12}O_{16}$ (1191.6050). The 67.5 MHz $^{13}$C NMR spectrum of janthinocin B in deuterated acetonitrile-deuterated water (1 4) is shown in FIG. 7. The ratio of janthinocin $B_1$:$B_2$ in this sample is approximately 3:1. The 400 MHz $^1$H NMR spectrum of janthinocin B ($B_2$:$B_1$ approximately 4:1) in deuterated acetonitrile-deuterated water (1:1, pH 7.1 with $Na_2DPO_4$) is shown in FIG. 8. The 400 MHz $^1$H NMR spectrum of janthinocin B ($B_2$:$B_1$ approximately 1:4) in deuterated acetonitrile-deuterated water (4:1) is shown in FIG. 9. Thin layer chromatography of janthinocin B on MERCK SILICA-GEL-60 ™ using chloroform-methanol-70% aqueous ethanol, 7:3:5, gives an $R_f$ value of 0.35 for janthinocin $B_2$ and 0.39 for janthinocin $B_1$. High performance liquid chromatography of janthinocin B on a HAMILTON PRP-1 ™ column (15×4.1 mm), eluting with Buffer A at 1 ml/min, and monitoring the absorbance at 220 nm, gives a retention time of 1.74 min. for $B_1$ and 2.76 min. for $B_2$.

Figure 10:
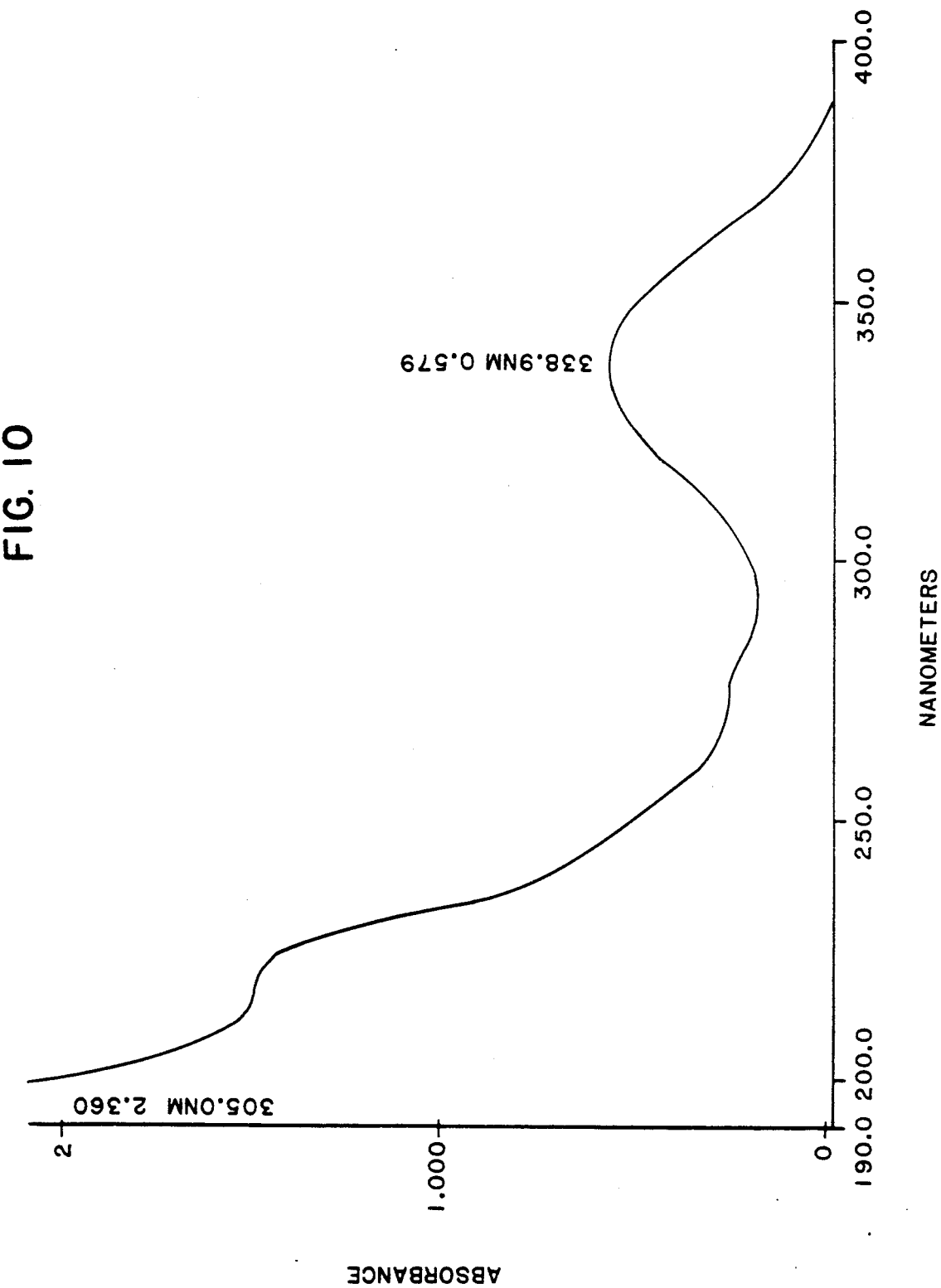
FIG. 10 shows the ultraviolet spectrum of janthinocin C in water.
Figure 11:
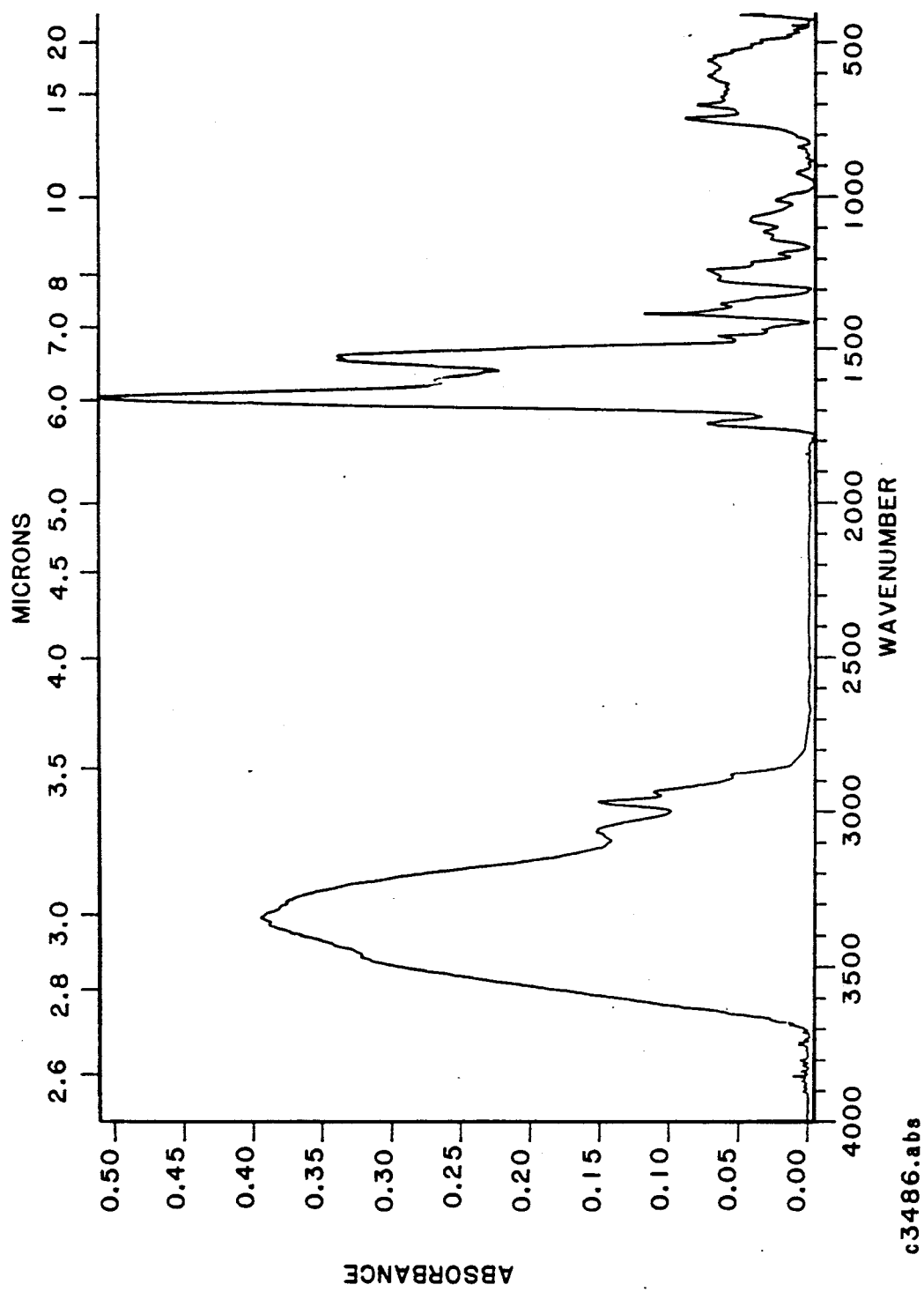
FIG. 11 shows the infrared spectrum of janthinocin C in potassium bromide.
Figure 12:
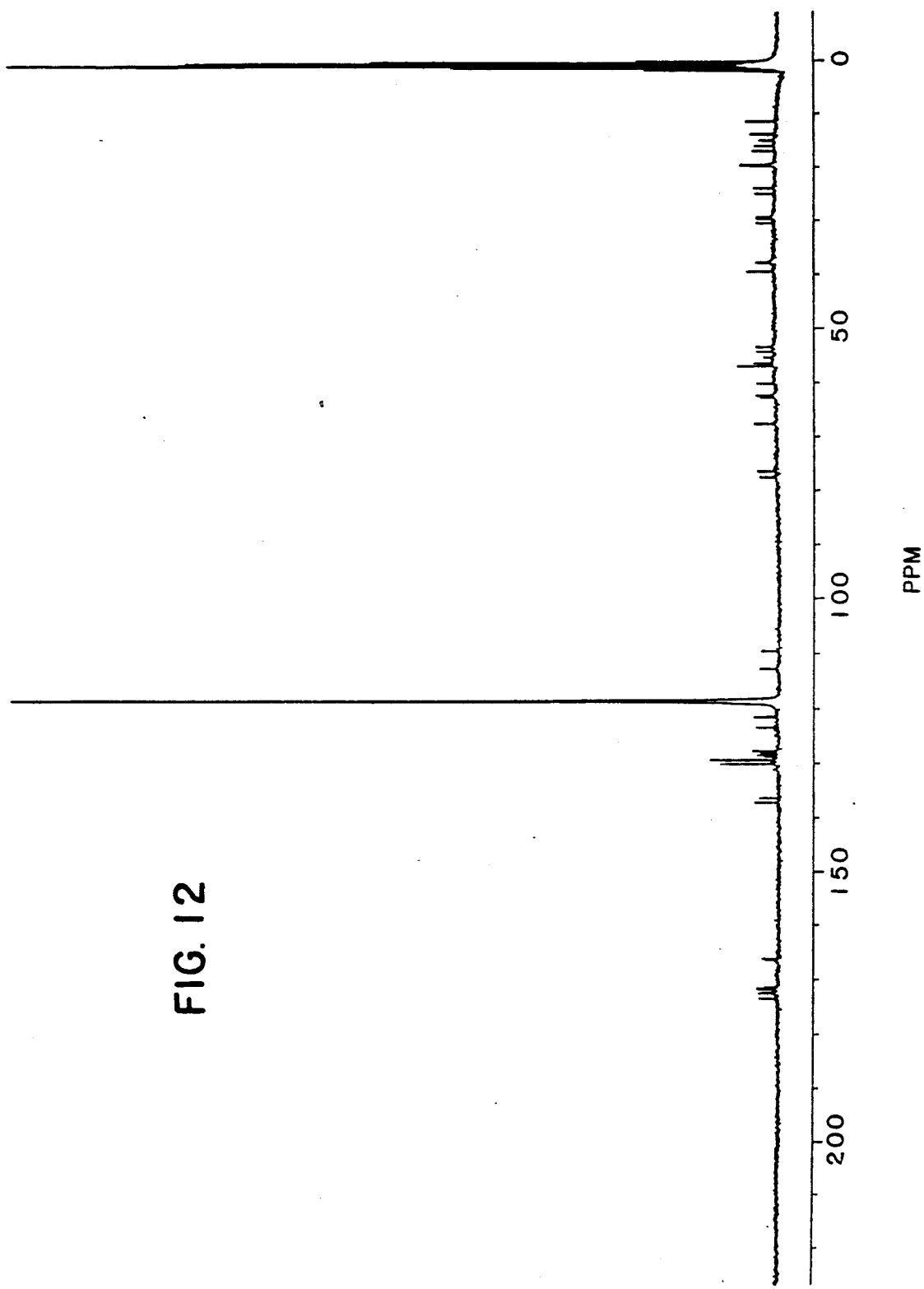
FIG. 12 shows the 67.5 MHz carbon NMR spectrum of janthinocin C in deuterated acetonitrile-deuterated water (4:1).
Figure 13:
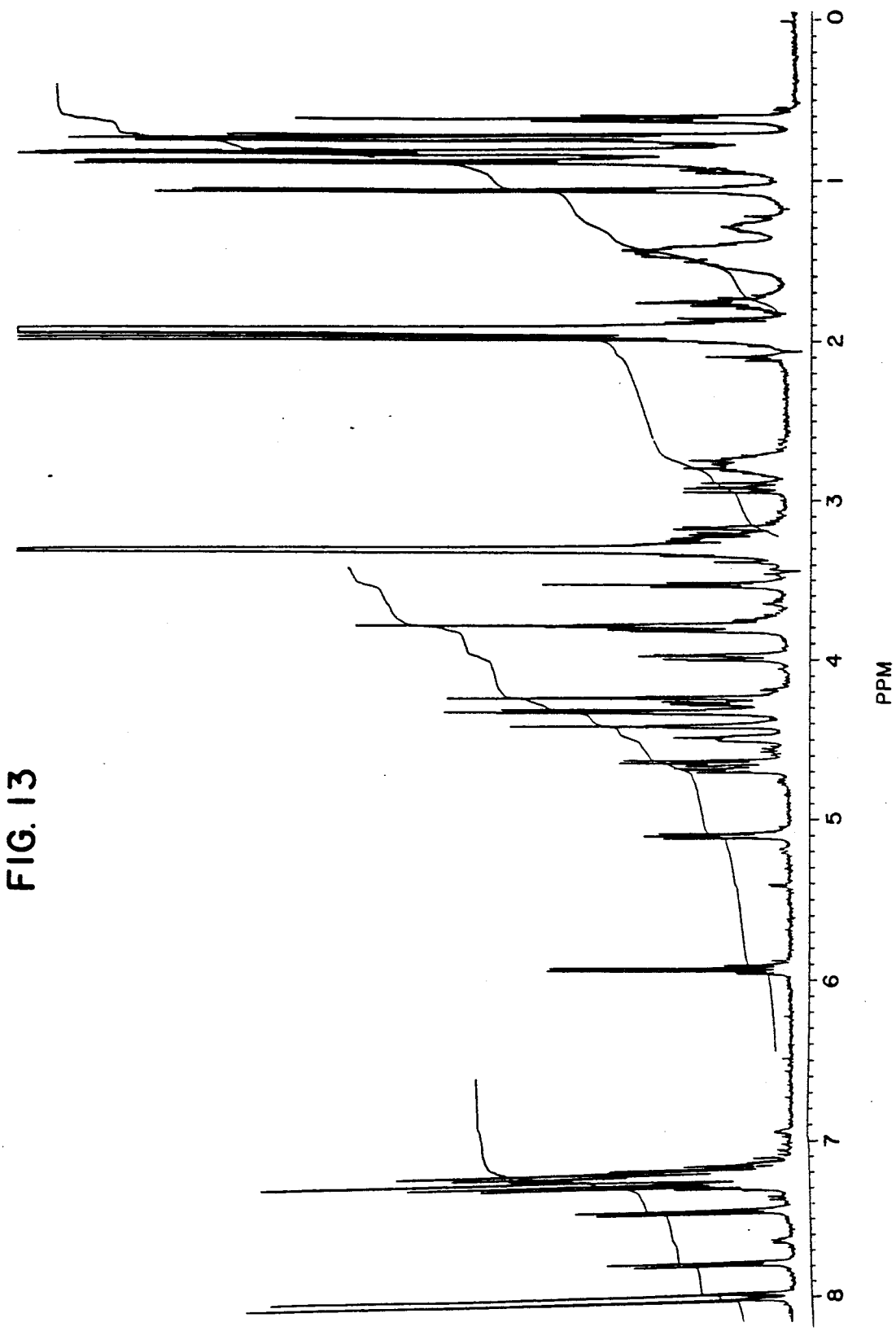
FIG. 13 shows the 400 MHz proton NMR spectrum of janthinocin C in deuterated acetonitrile-deuterated water (4:1).

The ultraviolet spectrum of janthinocin C is given in FIG. 10 and shows: λmax ($E^{1\%}$ 1 cm) 339(100), 220(250), 195 nm (400). The infrared spectrum of janthinocin C in potassium bromide is shown in FIG. 11. The following peaks are evident: 3342, 3066, 2968, 1744, 1654, 1602, 1526, 1384, cm$^{-1}$. The FAB mass spectrum janthinocin C in dithiothreitol-dithioerythritol-dimethylsulfoxide-glycerol shows the following ions: $(M+H)^+$ 1175, $(M-H)^-$ 1173 and the high resolution FAB mass spectrum shows an $(M+H)^+$ Of 1175.6205 consistent with the molecular formula $C_{57}H_{83}N_{12}O_{15}$ (1171.6101). The 67.5 MHz $^{13}$C NMR spectrum of janthinocin C in deuterated acetonitrile-deuterated water (4:1) is shown in FIG. 12. The 400 MHz $^1$H NMR spectrum of janthinocin C in deuterated acetonitrile-deuterated water (4:1) is shown in FIG. 13. Thin layer chromatography of janthinocin C on MERCK SILICA-GEL-60 ™ using chloroform-methanol-70% aqueous ethanol, 7:3:5, gives an $R_f$ value of 0.37. (janthinocin C is not resolved from $B_1$ when both are present.) High performance liquid chromatography of janthinocin C on a HAMILTON PRP-1 ™ column (150×4.1 mm), eluting with Buffer A at 1 ml/min and monitoring the absorbance at 220 nm, gives a retention time of 2.06 min.

Compounds of Formula I, and pharmaceutically acceptable salts thereof, can be used as agents to combat bacterial infections (particularly Gram-positive infections) in mammalian species, such as domesticated animals (e.g., dogs, cats, cows, horses and the like) and humans. They can be administered using modes of administration which have been used in the past to deliver penicillins and cephalosporins to the site of the infection. Such methods of administration include intravenous, intramuscular and as a suppository. The dosage of the antibiotic of formula I used will, of course, vary with the particular antibiotic, the size of the host and the severity of the infection. For a human adult, daily doses of about 250 milligrams to about 2 grams are exemplary. Further information about the potency of the compounds of this invention is set forth below under the heading "Biological Activity".

The following examples further illustrate the preparation and utility of janthinocin.

EXAMPLE 1

*Janthinobacterium lividum* was maintained on the following sterilized medium (A):

|  | Grams |
| --- | --- |
| Yeast extract | 5.0 |
| Glucose | 5.0 |
| $MgSO_4.7H_2O$ | 0.1 |
| $FeSO_4.7H_2O$ | 0.1 |
| Soil extract filtrate* | 200 ml |
| Agar | 17.5 |
| Tap $H_2O$ | 800 ml |

Media was sterilized at 121° C. for 15 minutes.
*Soil extract filtrate-1 vol soil + 2 vols. $H_2O$ extracted at 100 C. for 1 hour and filtered.

A loopful of surface growth from an agar slant (medium A) of *Janthinobacterium lividum* was used to inoculate each of three 500 ml Erlenmeyer flasks each containing 100 ml of the following sterilized medium (B):

|  | Grams |
| --- | --- |
| Yeast extract | 5.0 |
| Glucose | 5.0 |
| $MgSO_4.7H_2O$ | 0.1 |
| $FeSO_4.7H_2O$ | 0.1 |
| Tap $H_2O$ to 1 liter |  |

Media was sterilized at 121° C. for 15 minutes.

After inoculation, the flasks were then incubated at 25° C. on a rotary shaker (300 rpm; 2 inch stroke) for approximately 96 hours with a resulting broth pH of 8.0-8.5. After the appropriate incubation, as described above, 2% (vol/vol) transfers were made from the grown culture flasks to two hundred 500 ml Erlenmeyer flasks each containing 100 ml of sterilized medium (B) as described above. After inoculation, the flasks were once again incubated at 25° C. on a rotary shaker (as previously described) for approximately 24-28 hours with a resulting broth pH of 7.1-7.5. $(NH_4)_2SO_4$ (5 kg, 25% wt/vol) was added to the pooled broth (approx. 19-20 l) and the mixture was stirred for one hour. The broth($NH_4)_2SO_4$ mixture was then centrifuged and the supernate discarded. The pellet (800-900 g) was extracted with methanol (2.5 L, 1.5 hours) and the mixture again centrifuged. The methanol supernate was made approximately 10% aqueous by addition of 0.2 L of water, and then extracted with 0.8 L of carbon tetrachloride. The layers were separated, and the upper layer added to 0.6 L of water and 0.6 L of CHP20P. This was stirred for 1 hour and the resin collected by vacuum filtration. The charged resin was washed (in the funnel) with 2 L of methanol, 1 L of water and 2 L of $CH_3CN$. The charged resin was then packed in a column (5×50 cm) and the active components eluted as a purple band (60 ml) at the acid front with $CH_3CN-H_2O-HCO_2H$, 70:30:1. These fractions were taken to dryness in vacuo (109.2 mg). This material, a mixture of janthinocin A and B, as well as other impurities, was chromatographed on a 2.5×23 cm SEPHADEX LH-20 ™ column in $CH_3CN-H_2O$, 8:2. The active components co-eluted between 105 and 180 ml. The active effluent was concentrated in vacuo to give 53.5 of material. Partial resolution of janthinocin A and B was achieved by chromatography on CHP20P (1.5×34 cm, 2 ml/min) eluting with a linear gradient prepared from $CH_3CN-H_2O-HCO_2H$, 20:80:0 and 60:40:1 (220 g each), Fractions containing predominately janthinocin B (eluting between 138 and 152 ml) or janthinocin A (eluting between 166 and 192 ml) were pooled separately and concentrated to dryness in vacuo to give 5.5 mg of crude janthinocin B and 22.8 mg of crude janthinocin A.

EXAMPLE 2

Final purification of crude janthinocin A (84.8 mg), obtained from 60 L of broth as decribed in Example 1, was achieved by a repetition of the chromatography on CHP20P (1.5×36 cm, 2 ml/min) with a linear gradient of $CH_3CN-H_2O-HCO_2H$, 20:80:0 to 60:40:1 (225 g each). Janthinocin A eluted between 124 and 148 ml, and was nicely separated from a small amount of janthinocin B and also a yellow impurity. The active fractions were taken to dryness in vacuo, the residue dissolved in 0.5 ml of water, and $CH_3CN$ was added until a precipitate forms. Once again the solvent was removed in vacuo to give 58.5 mg of janthinocin A as an off-white powder.

EXAMPLE 3

The partially purified janthinocin B (5.5 mg) obtained from chromatography on CHP20P (described in Example 1), was combined with comparable material (101.1 mg) from earlier fermentations. Final purification was achieved by a repetition of the chromatography on CHP20P (2.5×35 cm) with a linear gradient prepared from $CH_3CN-H_2O-HCO_2H$, 20:80:0 and 60:40:1 (640 g each). janthinocin B eluted between 250 and 376 ml. The active fractions were combined and concentrated to dryness in vacuo. janthinocin B was obtained as an off white powder by dissolving the dried residue in a minimum amount of water, adding $CH_3CN$ until a precipitate formed and concentrating the sample to dryness in vacuo (86.1 mg).

EXAMPLE 4

Crude antibiotic obtained from several 20 L fermentations as described in Example 1, that contained both janthinocin B (a mixture of $B_1$ and $B_2$) and C (125.1 mg) was suspended in a buffer made by adding 3.3 ml of $CH_3CN$ to a solution of 6.7 ml of water and 0.1 g of $(NH_4)_2HPO_4$ adjusted to pH 7.1 with 85% $H_3PO_4$. The pH of this sample was adjusted to 3.6 with 85% $H_3PO_4$ immediately before chromatography on CHP20P eluting with Buffer A (50 ml), followed by a linear gradient of Buffer A to Buffer B (220 g each). Buffer A was made by adding 330 ml of $CH_3CN$ to a solution of 670 ml of $H_2O$ and 10.0 g of $NH_4H_2PO_4$, adjusted to pH 3.6 with 85% $H_3PO_4$. Buffer B was made by adding 600 ml of $CH_3CN$ to a solution of 400 ml of $H_2O$ and 10.0 g of $NH_4H_2PO_4$, adjusted to pH 3.6 with 85% $H_3PO_4$. janthinocin C eluted between 63 and 75 ml while janthinocin $B_2$ eluted between 150 and 225 ml. The activities were pooled separately and taken to dryness in vacuo.

Each was partially desalted by partitioning between BuOH—H$_2$O (3 times, 3 ml each of BuOH and H$_2$O), combining the BuOH layers, and taking them to dryness in vacuo, giving 44.8 mg of janthinocin B (as, a mixture of B$_1$ and B$_2$) and 39.5 mg of janthinocin C. Final purification was achieved by desalting on CHP20P (1.5×20 cm) eluting with a linear gradient of CH$_3$CN—H$_2$O—HCO$_2$H, 20:80:0 to 60:40:1 (120 g each), to give 37.0 mg of janthinocin B. Desalting of a combined pool of like samples of janthinocin C (94.1 mg) gave 53.5 mg of pure material.

Biological Activity

The following methodology was used to determine the minimum inhibitory concentration (hereinafter referred to as MIC) of the compound of this invention.

The aerobic test organisms were grown in approximately 15-20 ml of ANTIBIOTIC ASSAY BROTH TM (Difco) by inoculating (in tubes) the broth with a loopful of the organism from a BHI (Difco) agar slant. The inoculated tubes were incubated at 37° C. for 18 to 24 hours. These cultures are assumed to contain 10$^9$ colony forming units (CFU) per ml. The cultures were diluted 1:100 to give a final inoculum level of 10$^7$ CFU; dilutions were made with YEAST BEEF BROTH TM (Difco).

Janthinocin was dissolved in an appropriate diluent at a concentration of 1,000 μg/ml. Two-fold dilutions were made in YEAST BEEF BROTH TM (Difco), resulting in a range from 1000 μg/ml to 0.05 μg/ml. 1.5 ml of each dilution was placed into individual petri dishes to which 13.5 ml of K-10 agar was added. The composition of K-10 agar was:

| | Grams |
|---|---|
| Beef extract | 1.5 |
| Yeast extract | 3.0 |
| Peptone | 6.0 |
| Dextrose | 1.0 |
| Agar | 15.0 |
| Distilled water q.s. to 1 liter. | |

The final drug concentration in the agar ranged from 100 μg/ml to 0.05 μg/ml. Organism growth control plates containing agar only were prepared and inoculated before and after the test plates. The organisms were applied to the agar surface of each plate with a DENLY MULTIPOINT INOCULATOR TM (which delivers approximately 0.001 ml of each organism) resulting in a final inoculum of 10$^4$ CFU on the agar surface.

The plates were incubated at 37° C. for 18 hours and the MICs determined. The MIC was the lowest concentration of compound inhibiting growth of the organism.

The results of the agar dilution assays are as follows:

TABLE 1

| Organism | SC No.* | Janthinocin A MIC (μg/ml) | Janthinocin B MIC (μg/ml) | Janthinocin C MIC (μg/ml) |
|---|---|---|---|---|
| Staphylococcus aureus | 1276 | 0.8 | 0.4 | 1.6 |
| Staphylococcus aureus | 2399 | 1.6 | 1.6 | 3.1 |
| Staphylococcus aureus | 2400 | 1.6 | 1.6 | 3.1 |
| Staphylococcus aureus | 10165 | 1.6 | 0.8 | 1.6 |
| Streptococcus faecalis | 9011 | 1.6 | 1.6 | 12.5 |
| Streptococcus agalactiae | 9287 | 0.2 | <0.05 | 0.8 |
| Micrococcus luteus | 2495 | 0.2 | 0.2 | 1.6 |
| Escherichia coli | 8294 | 25 | 25 | >100 |
| Escherichia coli | 10857 | 12.5 | 12.5 | 50 |
| Escherichia coli | 10896 | 6.3 | 6.3 | 50 |
| Escherichia coli | 10909 | 6.3 | 6.3 | 25 |
| Klebsiella aerogenes | 10440 | 25 | 50 | 100 |
| Klebsiella pneumoniae | 9527 | 25 | 25 | >100 |
| Proteus mirabilis | 3855 | 100 | 100 | >100 |
| Proteus rettgeri | 8479 | 50 | 100 | >100 |
| Proteus vulgaris | 9416 | 12.5 | 12.5 | >100 |
| Salmonella typhosa | 1195 | 12.5 | 12.5 | 100 |
| Shigella sonnei | 8449 | 12.5 | 12.5 | 100 |
| Enterobacter cloacae | 8236 | 25 | 50 | >100 |
| Enterobacter aerogenes | 10078 | 25 | 50 | >100 |
| Citrobacter freundii | 9518 | 25 | 25 | 100 |
| Serratia marcescens | 9783 | 25 | 50 | >100 |
| Pseudomonas aeruginosa | 9545 | 50 | 50 | >100 |
| Pseudomonas aeruginosa | 8329 | 100 | 100 | >100 |
| Acinetobacter calcoaceticus | 8333 | 12.5 | 25 | 25 |

*SC No. is the number of the microorganism in the collection of E. R. Squibb & Sons, Inc., Princeton, New Jersey.

TABLE 2

| Organism | SC No.* | Janthinocin A MIC (μg/ml) | Janthinocin B MIC (μg/ml) |
|---|---|---|---|
| Bacillus subtilis | 3777 | 0.4 | 0.1 |
| Staphylococcus epidermidis (Penicillin$^S$)*** | 9052 | 0.8 | 0.4 |
| Staphylococcus epidermidis (Penicillin$^R$)** | 9083 | 0.8 | 0.4 |
| Staphylococcus epidermidis (Penicillin$^R$) | 9087 | 0.8 | 0.4 |
| Staphylococcus epidermidis (Penicillin$^R$) | 9607 | 0.4 | 0.4 |
| Staphylococcus epidermidis (Penicillin$^R$) | 10547 | 0.8 | 0.4 |
| Staphylococcus saprophyticus | 12875 | 0.8 | 0.4 |
| Staphylococcus aureus (Penicillin$^S$) | 2399 | 0.8 | 0.4 |
| Staphylococcus aureus (Tetracycline$^R$) | 10016 | 0.2 | 0.4 |
| Staphylococcus aureus (Penicillin$^R$) | 2400 | 0.4 | 0.8 |
| Staphylococcus aureus (Penicillin$^R$) | 9593 | 0.8 | 0.4 |
| Staphylococcus aureus | 9998 | 0.8 | 0.1 |

TABLE 2-continued

| Organism | SC No.* | Janthinocin A MIC (μg/ml) | Janthinocin B MIC (μg/ml) |
|---|---|---|---|
| (Penicillin^R) | | | |
| Staphylococcus aureus (Methicillin^R) | 3184 | 1.6 | 0.4 |
| Staphylococcus aureus (Methicillin^R) | 10014 | 0.4 | 0.4 |
| Staphylococcus aureus (Methicillin^R) | 10020 | 0.4 | 0.4 |
| Staphylococcus aureus (Gentamicin^R) | 11239 | 0.8 | 0.2 |
| Staphylococcus aureus (Erythromycin^R) | 10820 | 0.8 | 0.2 |
| Staphylococcus aureus (Erythromycin^R) | 12691 | 0.4 | 0.4 |
| Streptococcus faecalis | 9011 | 0.8 | 1.6 |
| Streptococcus faecalis | 9376 | 0.8 | 1.6 |
| Streptococcus faecalis | 10938 | 1.6 | 0.8 |
| Streptococcus agalactiae | 9285 | 0.4 | <0.05 |
| Streptococcus agalactiae | 9287 | 0.4 | <0.05 |
| Nocardia asteroides | 2626 | 0.8 | 3.1 |
| Nocardia monocytogenes | 8523 | 0.8 | 1.6 |

*SC No. is the number of the microorganism in the collection of E. R. Squibb & Sons, Inc., Princeton, New Jersey.
**(^R) indicates that the organism is resistant to the antibiotic named.
**(^S) indicates that the organism is sensitive to the antibiotic named.

The susceptibility of a number of anaerobic bacteria to a mixture of janthinocins A and B was also determined by an agar dilution technique. Test organisms were prepared from 24-48 hour cultures grown in CHOPPED MEAT BROTH ™ (Scott Laboratories, Fiskeville, R.I.), or from washings from chocolate agar slants. These slants were prepared by adding hemoglobin to Protease #3 agar (Difco) to a concentration of 1 percent. The growth was washed off the slants with BRAIN HEART INFUSION BROTH ™ (BBL Microbiology Systems) and diluted to a density of $1\times10^8$ CFU/ml. The trifluoroacetate salt of a mixture of janthinocins A and B was dissolved in the appropriate diluent at a concentration of 1,000 μg/ml. Two fold dilutions were made in YEAST BEEF BROTH ™ (Difco) resulting in a range from 1,000 μg/ml to 0.5 μg/ml. A 1.5 ml sample of each dilution was placed into individual petri dishes to which 13.5 ml of DST agar (Oxoid USA, Inc. Red Branch Road, Columbia, Md.) containing 5% lysed sheep blood and 0.5 μg/ml vitamin K was added. The final drug concentration in the agar ranged from 100 μg/ml to 0.05 μg/ml. Organism growth control plates containing agar only were prepared and inoculated before and after the test plates. The organisms were applied to the surface of each plate with the DENLY MULTIPOINT INOCULATOR ™ (which delivers approximately 0.001 ml of each organism) resulting in a final inoculum level of $10^5$ CFU on the agar surface. Plates were incubated at 37° C. for 18 hours in an anaerobic chamber (Forma Scientific, Marietta, Ohio) and the MIC values then determined. The MIC is the lowest concentration of antibiotic inhibiting growth of the organism.

The results of the agar dilution assays are:

| Organism | SC No.* | Mixture of Janthinocin A and B MIC (μg/ml) |
|---|---|---|
| Bacteroides thetaiotaomicron | 9005 | 6.3 |
| Bacteroides fragilis | 9844 | 25.0 |
| Bacteroides fragilis | 10277 | 50.0 |
| Bacteroides thetaiotaomicron | 10278 | 25.0 |
| Bacteroides fragilis | 10279 | 25.0 |
| Bacteroides fragilis | 10280 | 50.0 |
| Bacteroides fragilis | 11085 | 50.0 |
| Bacteroides melaninogenicus | 12885 | — |
| Clostridium histolyticum | 8572 | 0.4 |
| Clostridium perfringens | 11256 | 0.4 |
| Clostridium septicum | 1780 | 0.2 |
| Clostridium sporogenes | 2372 | 0.05 |
| Clostridium difficile | 11251 | 50.0 |
| Hemophilus vaginalis | 8568 | 0.4 |
| Hemophilus vaginalis | 9640 | 0.1 |
| Bifidobacterium dentium | 11260 | 0.2 |
| Eubacterium lentum | 11261 | — |
| Fusobacterium necrophorum | 10338 | — |
| Peptococcus variabilis | 11264 | 0.8 |
| Peptostreptococcus anaerobius | 11263 | 0.8 |
| Propionibacterium acnes | 4020 | 0.4 |

*SC No. is the number of the microorganism in the collection of E. R. Squibb & Sons, Inc., Princeton, New Jersey.

What is claimed is:
1. A compound having the formula

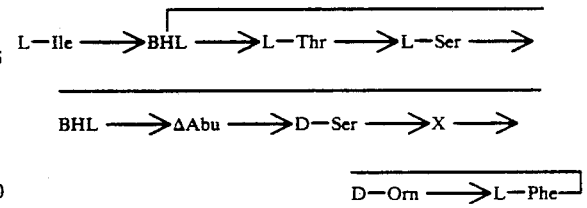

or a pharmaceutically acceptable salt thereof,
wherein Δ-Abu is dehydro-α-aminobutyric acid;
βHL is D-erythro-β-Hydroxyleucine; and,
X is β-hydroxytryptophan, β-ketotryptophan or dehydrotryptophan.

2. A compound in accordance with claim 1 wherein X is β-hydroxy-tryptophan.

3. A compound in accordance with claim 1 wherein X is β-keto-tryptophan.

4. A compound in accordance with claim 1 wherein X is dehydrotryptophan.

5. A compound, or a pharmaceutically acceptable salt thereof in accordance with claim 2, having the ultraviolet spectrum of FIG. 1, the infrared spectrum of FIG. 2, the 67.5 MHz carbon NMR spectrum of FIG. 3 and the 400 MHz proton NMR spectrum of FIG. 4.

6. A compound, or a pharmaceutically acceptable salt thereof in accordance with claim 3, having the ultraviolet spectrum of FIG. 5, the empirical formula $C_{57}H_{83}N_{12}O_{16}$, the infrared spectrum of FIG. 6, the 67.5 MHz carbon NMR spectrum of FIG. 7 and the 400 MHz proton NMR spectra of FIGS. 8 and 9.

7. A compound, or a pharmaceutically acceptable salt thereof in accordance with claim 4, having the ultraviolet spectrum of FIG. 10, the empirical formula $C_{57}H_{83}N_{12}O_{15}$, the infrared spectrum of FIG. 11, the 67.5 MHz carbon NMR spectrum of FIG. 12 and the 400 MHz proton NMR spectrum of FIG. 13.

* * * * *